US012560576B2

(12) United States Patent (10) Patent No.: US 12,560,576 B2
Yatsuda (45) Date of Patent: Feb. 24, 2026

(54) SENSOR SYSTEM AND METHOD FOR ESTIMATING AMOUNTS OF DIFFERENT MOLECULES IN BIOLOGICAL LIQUID

(71) Applicant: tst biomedical electronics Co., Ltd., Taoyuan (TW)

(72) Inventor: Hiromi Yatsuda, Taoyuan (TW)

(73) Assignee: TST BIOMEDICAL ELECTRONICS CO., LTD., Taoyuan (TW)

( * ) Notice: Subject to any disclaimer, the term of this patent is extended or adjusted under 35 U.S.C. 154(b) by 904 days.

(21) Appl. No.: 17/836,461

(22) Filed: Jun. 9, 2022

(65) Prior Publication Data

US 2022/0404313 A1 Dec. 22, 2022

Related U.S. Application Data

(60) Provisional application No. 63/210,614, filed on Jun. 15, 2021.

(51) Int. Cl.
| | |
|---|---|
| *G01N 29/02* | (2006.01) |
| *G01N 29/024* | (2006.01) |
| *G01N 29/036* | (2006.01) |
| *G01N 29/34* | (2006.01) |
| *G01N 33/487* | (2006.01) |
| *G01N 33/543* | (2006.01) |

(52) U.S. Cl.
CPC ......... *G01N 29/022* (2013.01); *G01N 29/024* (2013.01); *G01N 29/036* (2013.01); *G01N 29/348* (2013.01); *G01N 33/487* (2013.01);
*G01N 33/5438* (2013.01); *G01N 2291/022* (2013.01); *G01N 2291/0255* (2013.01); *G01N 2291/0423* (2013.01)

(58) Field of Classification Search
CPC .. G01N 29/022; G01N 29/024; G01N 29/036; G01N 29/348; G01N 33/487; G01N 33/5438; G01N 2291/022; G01N 2291/0255; G01N 2291/0423; G01N 29/4427; G01N 2291/02466; G01N 2291/0256
See application file for complete search history.

(56) References Cited

U.S. PATENT DOCUMENTS

| | | | | |
|---|---|---|---|---|
| 11,156,542 B2 * | 10/2021 | Shachar | ............... | G01N 29/222 |
| 2020/0253513 A1 * | 8/2020 | Zhou | .................. | A61B 5/14532 |

* cited by examiner

*Primary Examiner* — Tarun Sinha
(74) *Attorney, Agent, or Firm* — Volpe Koenig

(57) ABSTRACT

The present invention discloses a sensor system for estimating respective amounts of different molecules in a biological liquid, and the sensor system includes: an electronic circuit module and a Shear Horizontal Surface Acoustic Wave (SH-SAW) sensor, wherein the electronic circuit module has more than two different impedance matching circuits for exciting and detecting a plurality of Surface Acoustic Waves (SAWs) with different frequencies, and the SH-SAW sensor has at least one transducer and a surface on which the plurality of SAWs propagate, and wherein the surface is covered with a probe to be bound with more than two different molecules.

13 Claims, 16 Drawing Sheets

1

508

508

508

508

508

508

900

910

920

1000

$(V_1, A_1)$ $(V_2, A_2)$ $L_0$      $L_2(V_2, A_2)$      $L_1(V_1, A_1)$

2000

SENSOR SYSTEM AND METHOD FOR ESTIMATING AMOUNTS OF DIFFERENT MOLECULES IN BIOLOGICAL LIQUID

CROSS-REFERENCE TO RELATED APPLICATION AND CLAIM OF PRIORITY

This application claims priority to U.S. Provisional Patent Application No. 63/210,614, filed Jun. 15, 2021, which is incorporated herein in its entirety by reference.

FIELD OF THE INVENTION

The present invention is related to a sensor system for a biological liquid. In particular, the present invention is related to a sensor system for estimating amounts of different molecules in the biological liquid.

BACKGROUND OF THE INVENTION

Biochip is a chip designed to detect or quantify target analytes such as protein, DNA, cell, glucose, cardiovascular disease biomarker, cancer biomarker, bacteria and virus. Many biochips are affinity-based, which means that they use a fixed capture probe on a sensing surface to bind the target analyte, and characteristic changes caused by the interaction between the fixed capture probe and the target analyte on the sensing surface are detected by a reader.

There are various important requirements for a sensor system, such as portability, low cost per test, maximum achievable sensitivity and specificity, and ease of use. The shear horizontal surface acoustic wave (SH-SAW) immunoassay-based biosensors can be disposable, inexpensive and suitable for mass production, and thereby they have great market potential.

SH-SAW sensors use an antigen-antibody reaction to measure the concentration of antigens in a biological sample through changes in the propagation characteristics of the SH-SAW.

There are usually different target analytes in the biological sample. For example, there are different proteins or biomarkers in the blood. Take lipoproteins in the blood as an example, there are three main classifications: (i) high-density lipoprotein (HDL), (ii) low-density lipoprotein (LDL) and (iii) very low-density lipoprotein (VLDL). Different classes of lipoproteins (HDL, LDL and VLDL) play different roles concerning atherosclerosis. For example, HDL is considered to be anti-atherogenic, and LDL is highly atherogenic. If the SH-SAW sensor can be used to analyze different molecules in the biological sample in a simple operation, it will be very helpful to be aware of a disease in an earlier stage and monitor the progression of the disease.

In order to analyze different target analytes in a biological sample, it is usually necessary to perform detection procedures several times by changing different biochips when traditional biochips are used. The traditional biochip method not only consumes a lot of time, but also fails to achieve the desired analysis results when there is only a small amount of the biological sample.

Therefore, there is a need for a sensor system and a method that can efficiently analyze different molecules in the biological sample in a simple manner.

SUMMARY OF THE INVENTION

The present invention provides a sensor system for estimating amounts of different molecules in a biological liquid, wherein the amounts of different molecules can be estimated by an SH-SAW sensor in a single operation.

In one aspect, the present invention discloses a sensor system for estimating respective amounts of different molecules in a biological liquid, and the sensor system includes: an electronic circuit module and a Shear Horizontal Surface Acoustic Wave (SH-SAW) sensor, wherein the electronic circuit module has more than two different impedance matching circuits for exciting and detecting a plurality of Surface Acoustic Waves (SAWs) with different frequencies, and the SH-SAW sensor has at least one transducer and a surface on which the plurality of SAWs propagate, and wherein the surface is covered with a probe to be bound with more than two different molecules.

The present invention further discloses a sensor system for estimating respective amounts of different molecules in a biological liquid, and the sensor system includes a Shear Horizontal Surface Acoustic Wave (SH-SAW) sensor having at least two channels for a Surface Acoustic Wave (SAW) propagation, in which each channel includes: at least one transducer and a surface on which a plurality of SAWs propagate, wherein the surface is covered with a probe to be bound with more than two different molecules and has a respective thickness different from those of the remaining channels.

In another aspect, the present invention discloses a method for estimating respective amounts of different molecules in a biological liquid by using a Shear Horizontal Surface Acoustic Wave (SH-SAW) sensor, the method includes the steps of providing preconfigured velocity and/or amplitude related parameters of a plurality of Surface Acoustic Waves (SAWs) transmitted over the SH-SAW sensor for the different molecules respectively, causing the different molecules in the biological liquid to interact with the SH-SAW sensor, measuring velocity and/or amplitude related parameters of the plurality of SAWs for the SH-SAW sensor at different frequencies respectively for the SH-SAW sensor after an interaction of the SH-SAW sensor with the different molecules, and estimating the respective amounts of the different molecules using the preconfigured velocity and/or amplitude related parameters as well as the measured velocity and/or amplitude related parameters.

The present invention further discloses a method for estimating respective amounts of different molecules in a biological liquid by using a Shear Horizontal Surface Acoustic Wave (SH-SAW) sensor, wherein the SH-SAW sensor has at least two channels having different thicknesses, the method includes the steps of providing preconfigured velocity and/or amplitude related parameters of a plurality of Surface Acoustic Waves (SAWs) transmitted over the SH-SAW sensor for the different molecules in the at least two channels respectively, causing the different molecules in the biological liquid to interact with the SH-SAW sensor, measuring velocity and/or amplitude related parameters of the plurality of SAWs for the SH-SAW sensor in the at least two channels respectively after an interaction of the SH-SAW sensor with the different molecules, and estimating the respective amounts of the different molecules using the preconfigured velocity and/or amplitude related parameters as well as the measured velocity and/or amplitude related parameters.

BRIEF DESCRIPTION OF THE DRAWINGS

The objectives and advantages of the present invention will become more readily apparent to those ordinarily skilled in the art after reviewing the following detailed descriptions and accompanying drawings.

DETAILED DESCRIPTION OF THE PREFERRED EMBODIMENTS

The present invention will now be described more specifically with reference to the following embodiments. It is to be noted that the following descriptions of the preferred embodiments of this invention are presented herein for purpose of illustration and description only; they are not intended to be exhaustive or to be limited to the precise form disclosed.

The sensor system of the present invention is used to estimate the amounts of different molecules in a biological liquid. The term "biological liquid" as used herein refers the biological liquid such as urine, serum, whole blood, cell lysate, saliva, etc.

The term "molecule" as used herein refers to a protein or a biomarker presenting in the above biological liquid that can interact with a probe fixed on the sensor system, and includes but not limited to lipoprotein, cholesterol, acute phase reactant (such as C-reactive protein (CRP) and serum amyloid A (SAA)), antibody and cytokine, or other substances presenting in the biological liquid. The term "amount of the molecule" as used herein preferably refers to the concentration of the above-mentioned molecule in the biological liquid.

Figure 1:
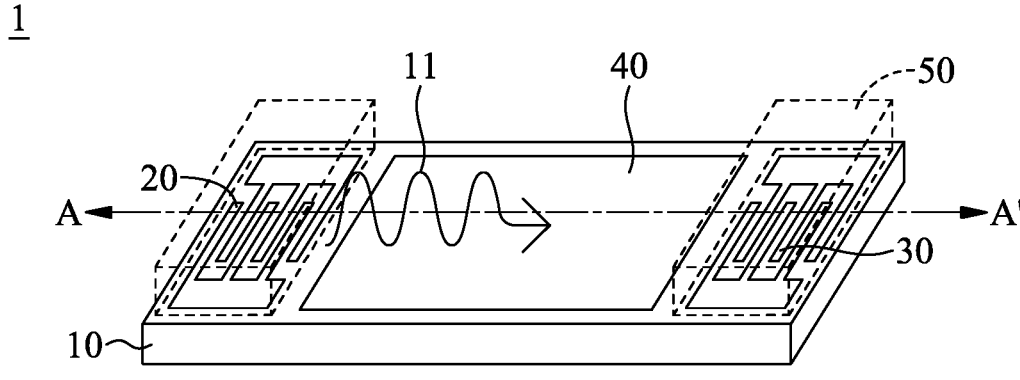
FIG. 1 is a perspective view of a SH-SAW sensor in the present invention.

FIG. 1 shows a Shear Horizontal Surface Acoustic Wave (SH-SAW) sensor 1 in the present invention, which is a delay line configuration including a piezoelectric substrate 10. A first SAW transducer 20, a second SAW transducer 30 and a metal surface 40 are formed on the piezoelectric substrate 10. The first SAW transducer 20 excites and emits SAWs 11. The emitted SAWs 11 propagate on the metal surface 40 between the first SAW transducer 20 and the second SAW transducer 30. The second SAW transducer 30 placed along the direction of SAW propagation at a defined distance from the first SAW transducer 20 receives the emitted SAWs 11 and converts the acoustic signal of the emitted SAWs 11 back to an electrical signal. Both of the first SAW transducer 20 and the second SAW transducer 30 are protected by a hollow structure or a cap 50. Sensor response is represented as shift in the SAW delay time, shift in the transmission loss, phase shift between the exciting and the receiving SAW transducers, or a combination thereof.

Figure 2:
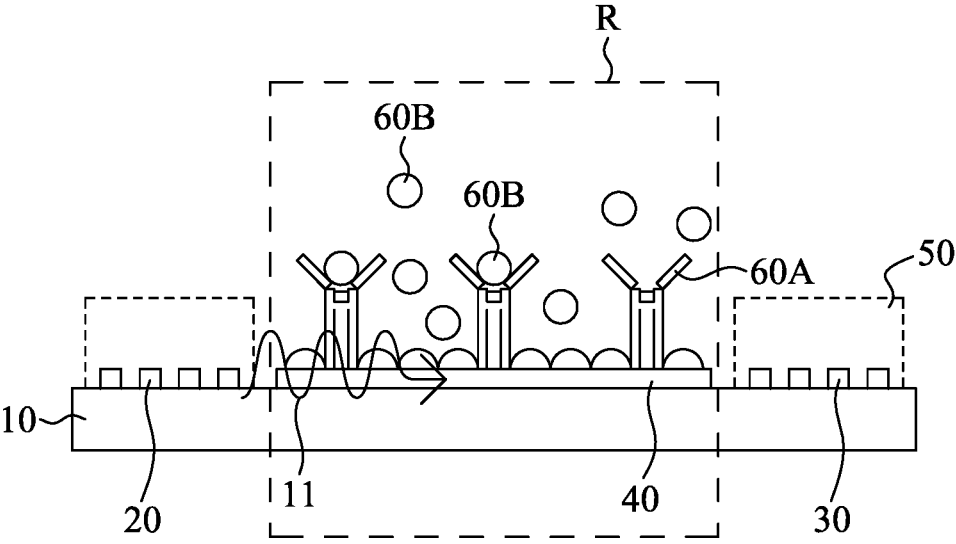
FIG. 2 is a cross-sectional view of FIG. 1 along Line A-A'.

FIG. 2 is a cross-sectional view of FIG. 1 along Line A-A'. To detect a target analyte 60B (such as an antigen) in the biological liquid, the metal surface 40 is coated with a probe 60A (such as an antibody) to bind the target analyte 60B. After the antigen-antibody reaction is completed, the propagation characteristics of the SAWs 11 on the metal surface 40 will change and can be measured.

Figure 3A:
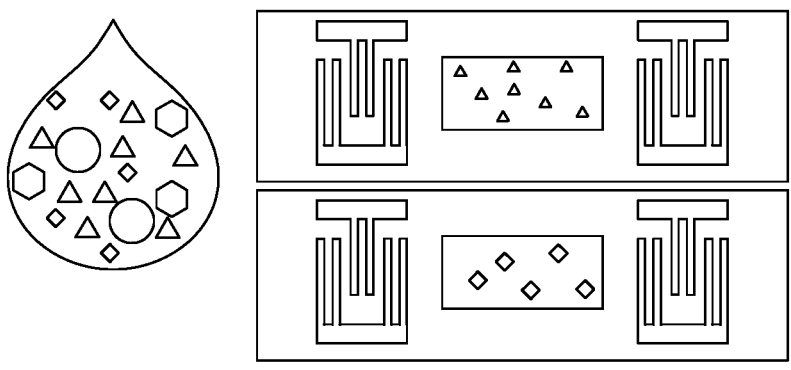
FIG. 3A is a schematic diagram of the estimating method in the prior art.
Figure 3B:
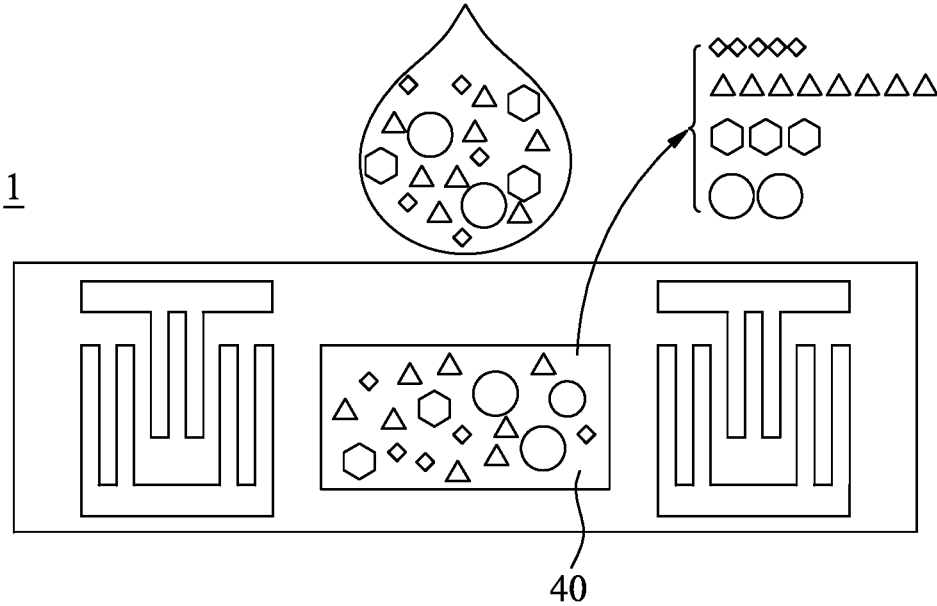
FIG. 3B is a schematic diagram of the estimating method in the present invention.

To estimate amounts of different molecules in the biological liquid, different antibodies are used to capture these different molecules. Conventionally, different antibodies are coated on the respective metal surface of the different SH-SAW sensors, as shown in FIG. 3A. By using the SH-SAW sensor 1 and the estimating method in the present invention, in which the different antibodies are coated on the same metal surface 40 of the SH-SAW sensor 1, the amounts of different molecules can be estimated in a single operation (as shown in FIG. 3B).

Figure 4:
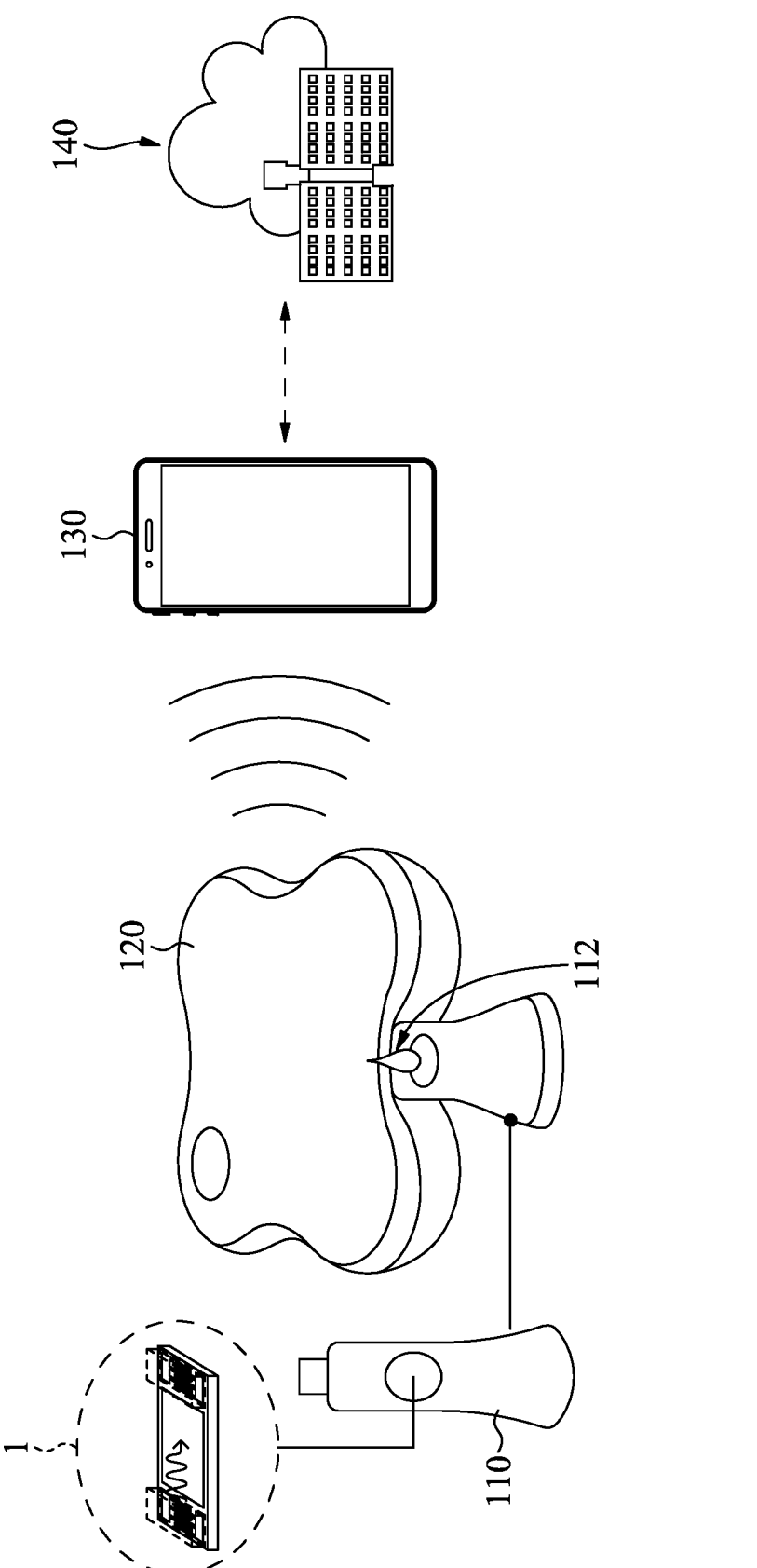
FIG. 4 is a schematic diagram of the sensor system in the present invention.

Please refer to FIG. 4, which is a schematic diagram of the sensor system 100 in the present invention. The sensor system 100 in the present invention includes a test cartridge 110 containing a SH-SAW sensor 1 inside, a reader 120, a user device 130 and a database 140. Before the detection is performed, the test cartridge 110 is coupled to the reader 120. A biological liquid 112 (such as urine, serum, whole blood, cell lysate or saliva) was taken from a subject. The biological liquid 112 was then applied on the metal surface 40 of the SH-SAW sensor 1 so that the molecules in the biological liquid 112 can interact with the probe fixed on the metal surface 40. The reader 120 can transmit and receive a plurality of SAWs with different frequencies so as to measure velocity and/or amplitude of the plurality of SAWs with different frequencies. The reader 120 sends the measuring or estimating results to the user device 130 such as a computer, a mobile phone or a tablet, which is connected to the reader 120 wirelessly or electrically. The user device 130 can send the measuring or estimating results to the database 140 to store the measuring or estimating results. Alternatively, the user device 130 can receive the referencing data from the database 140 to compare the measuring or estimating results with the referencing data. Although the database 140 is illustrated as a cloud database in FIG. 4, it is conceivable by a skilled person in the art that the database 140 can also be electrically connected to or integrated in the user device 130.

To estimate amounts of different molecules in a biological liquid, specific SH-SAW sensors that can excite and detect a plurality of SAWs with different frequencies are provided in the present invention as follows.

Figure 5A:
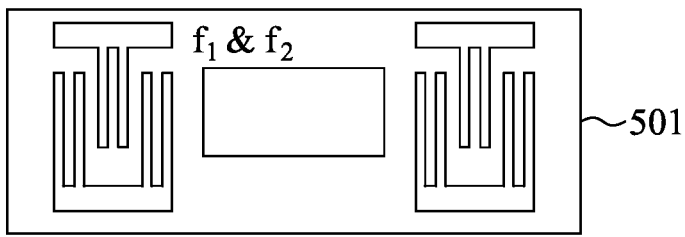
FIGS. 5A-5C are schematic diagrams of the SH-SAW sensor according to the preferred embodiments of the present invention.
Figure 5B:
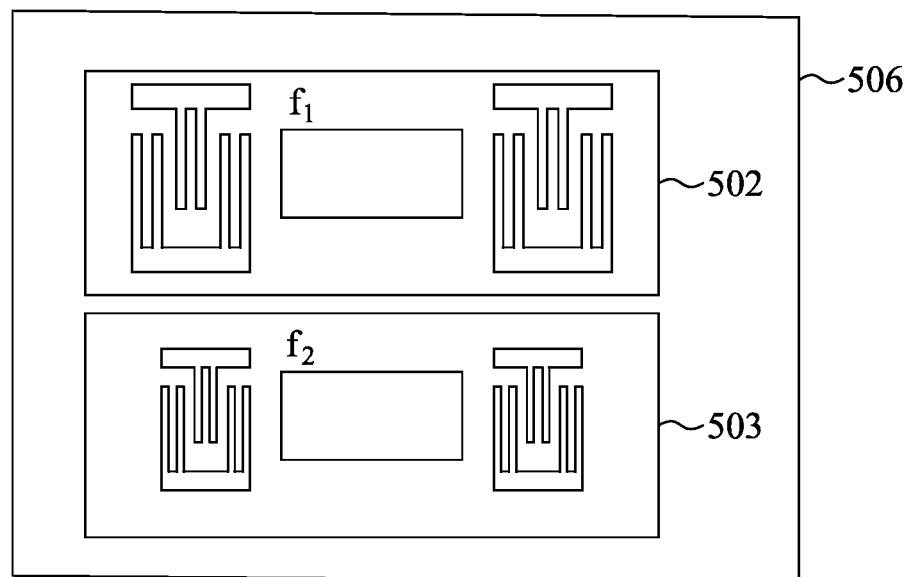
Figure 5C:
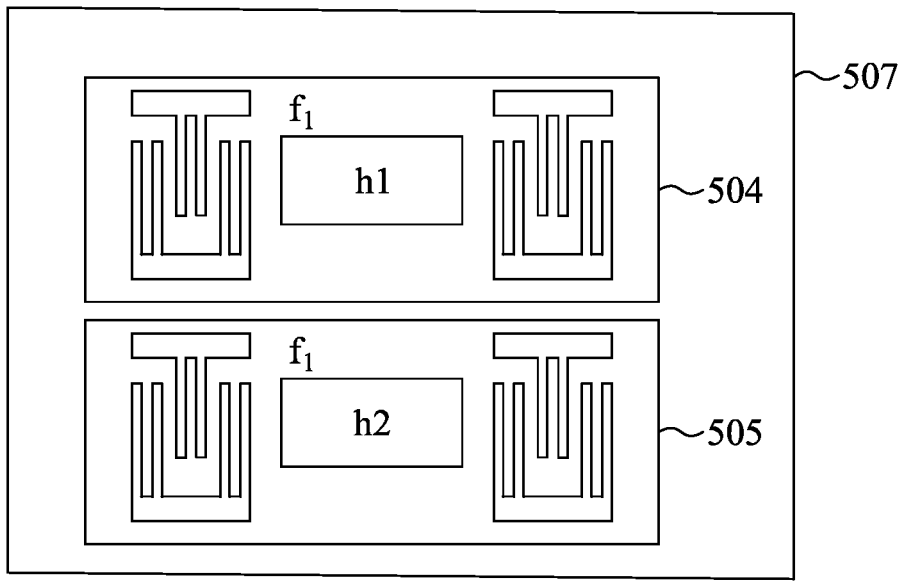

Please refer to FIGS. 5A-5C, which show three preferred embodiments of the SH-SAW sensors in the present invention.

1. Single Channel SH-SAW Sensor

FIG. 5A shows a single channel SH-SAW sensor 501 including two transducers disposed on two opposite ends along a propagation direction of the plurality of SAWs, and a metal surface between the two transducers, wherein a plurality of SAWs with different frequencies ($f_1$, $f_2$) propagate on the metal surface.

Figure 7A:
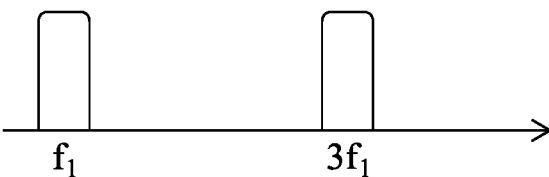
FIG. 7A is a diagram showing different frequencies modulated by a four fingers interdigital transducer (4F-IDT).
Figure 7B:
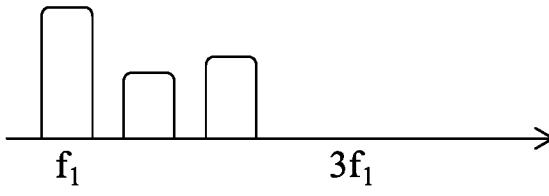
FIG. 7B is a diagram showing different frequencies modulated by a withdrawal weighted IDT.
Figure 7C:
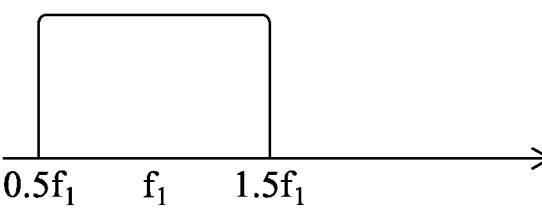
FIG. 7C is a diagram showing different frequencies modulated by an apodized weighted IDT.

Preferably, the transducer used in the present invention is an interdigital transducer (IDT). Specifically, the transducer used in the single channel SH-SAW sensors in the present invention may be a four fingers interdigital transducer (4F-IDT), a withdrawal weighted IDT or an apodized weighted IDT. Please refer to FIGS. 7A-7C, which show the examples of different frequencies for the single channel SH-SAW sensor 501. For example, 4F-IDT and withdrawal weighted IDT, which have multi-band characteristics and can operate at different frequencies as shown in FIGS. 7A and 7B, respectively, may be used in the single channel SH-SAW sensor 501. In one preferred embodiment, the 4F-IDT can operate at frequencies $f_1$ and $3f_1$. Alternatively, apodized weighted IDT, which has wide-band characteristics and can operate at different frequencies as shown in FIG. 7C, may also be used in the single channel SH-SAW sensor 501. In one preferred embodiment, the apodized weighted IDT can operate at frequencies between $0.5f_1$ and $1.5f_1$. Preferably, the different frequencies differ from one another by more than 5% in Hz.

2. Multi-Channel SH-SAW Sensor with Different Frequencies

Figure 7D:
FIG. 7D is a diagram showing an example of different frequencies for the multi-channel SH-SAW sensor.
Figure 7D:
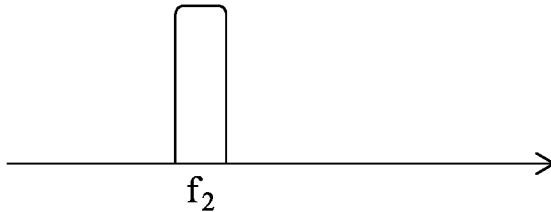

FIG. 5B shows a multi-channel SH-SAW sensor 506 including a first channel 502 and a second channel 503, wherein each channel includes two transducers and a metal surface between the two transducers. As shown in FIG. 5B, the plurality of SAWs with a first frequency ($f_1$) propagate on the first channel 502, and the plurality of SAWs with a second frequency ($f_2$) propagate on the second channel 503. An example of different frequencies ($f_1$, $f_2$) is shown in FIG. 7D. The term "frequencies $f_1$ and $f_2$" used herein should be interpreted as different frequencies, and the frequencies ($f_1$, $f_2$) shown in FIG. 7D is merely an example of different frequencies, which does not indicate the frequencies $f_1$ and $f_2$ mentioned in the embodiments of the present invention.

3. Multi-Channel SH-SAW Sensor with Different Thicknesses

Figure 7E:
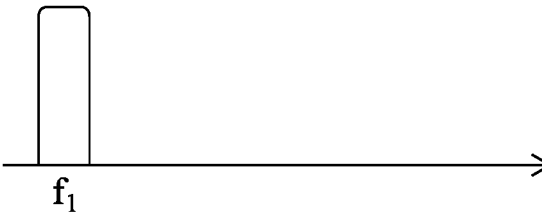
FIG. 7E is a diagram showing an example of a specific frequency for the multi-channel SH-SAW sensor with different thicknesses.
Figure 7E:

The multi-channel SH-SAW sensor 507 including a first channel 504 and a second channel 505 in FIG. 5C has a configuration similar to that in FIG. 5B, however, the plurality of SAWs with the same frequency ($f_1$) propagate on the first channel 504 and the second channel 505, and the metal surface on each channel has a respective thickness (h1, h2). The example of the frequency $f_1$ is shown in FIG. 7E.

Figure 5D:
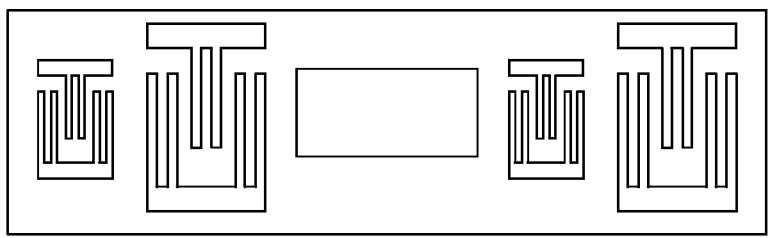
FIG. 5D shows an alternative modification of the SH-SAW sensor in FIG. 5A.

In an alternative embodiment, the transducer in the present invention may include two or more IDTs with different center frequencies located in series on the propagation direction. Each of these two or more IDTs with different center frequencies can operate at a specific frequency. For example, the single channel SH-SAW sensor 501 with an IDT having multi-band characteristics in FIG. 5A can be modified as another single channel SH-SAW sensor with two IDTs with different center frequencies, as shown in FIG. 5D.

Figure 5E:
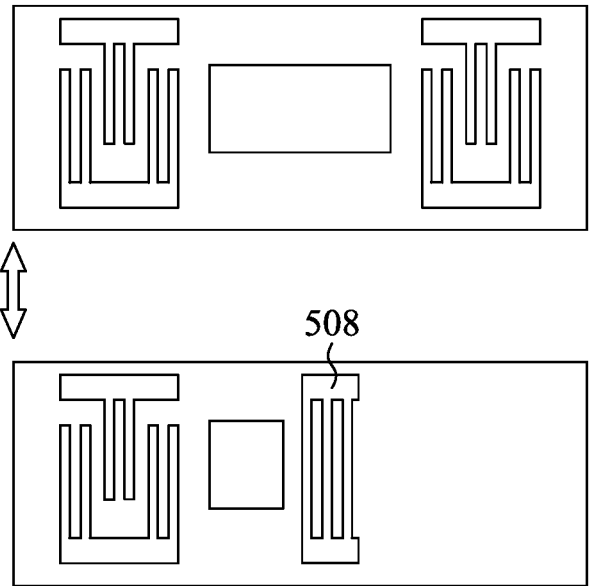
FIG. 5E is a schematic diagram showing two equivalent configurations of the SH-SAW sensor.

FIG. 5E shows two equivalent configurations of the SH-SAW sensor. Conventionally, the SH-SAW sensor has two transducers. In FIG. 5E, the transducer on the output end (right side) can be replaced by a reflector 508. That is to say, the SH-SAW sensors in FIGS. 5A-5C can be configured as those in FIGS. 6A-6C, respectively. In the SH-SAW sensors shown in FIGS. 6A-6C, each channel includes at least one transducer and a reflector 508. In the reflected type SH-SAW sensors in FIGS. 6A-6C, the plurality of SAWs are reflected by the reflector 508, and then converted into electrical signals by the transducer.

Figure 6A:
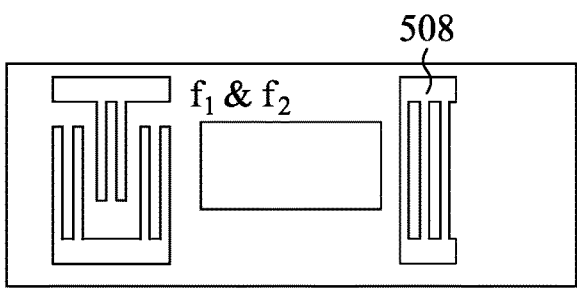
FIGS. 6A-6C are schematic diagrams of the SH-SAW sensor according to respective equivalent configurations for each of the SH-SAW sensors in FIGS. 5A-5C.
Figure 6B:
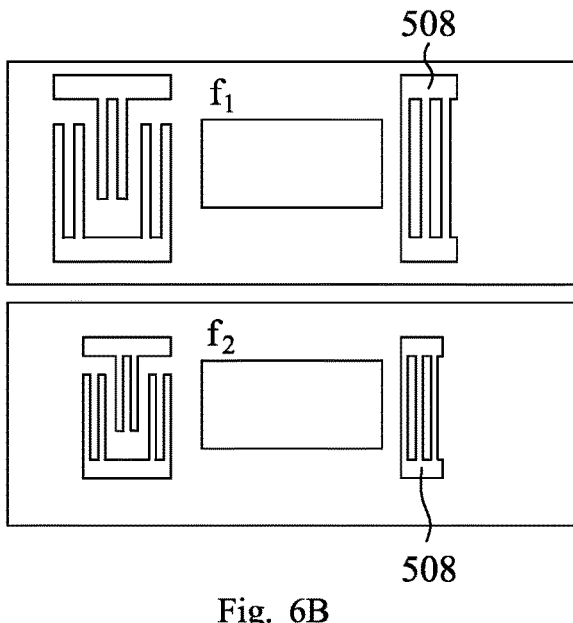
Figure 6C:
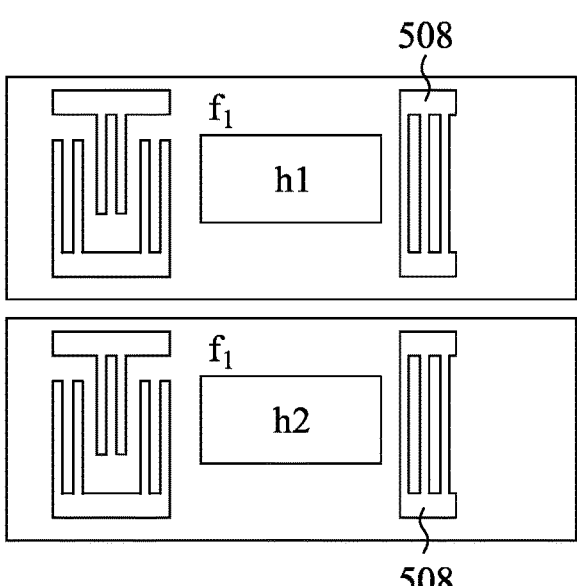

The SH-SAW sensor in the present invention can be configured with or without a reference channel. For example, the single channel SH-SAW sensors as shown in FIGS. 5A and 6A may include an additional reference channel, and the multi-channel SH-SAW sensors as shown in FIGS. 5B, 5C, 6B and 6C may include one or two additional reference channels. In the presence of the reference channel, some kinds of measurement errors can be compensated. However, the SH-SAW sensor in the present invention can work without the reference channel.

The detailed components in each configuration of the SH-SAW sensors in the present invention will be described in the following.

In the SH-SAW sensors in the present invention, to enable the IDT to operate at different frequencies, it is necessary to couple the SH-SAW sensor with an electronic circuit module. Please refer to FIG. 8A to FIG. 8D, which show various electronic circuit modules 800, 810, 820, 830 for the single channel SH-SAW sensors. According to the present invention, the electronic circuit module has more than two impedance matching circuits for exciting and detecting SAWs with different frequencies, wherein each electronic circuit module is exemplarily illustrated as having two impedance matching circuits (hereinafter referred to as matching circuits) in FIG. 8A to FIG. 8D. Optionally, the electronic circuit module in the present invention further includes a switch to select the more than two different matching circuits for the different frequencies. Although not explicitly depicted in the figures, it is well known in the art that the reflectors in FIGS. 8A to 8D can be designed to have different pitches for different frequencies.

Figure 8A:
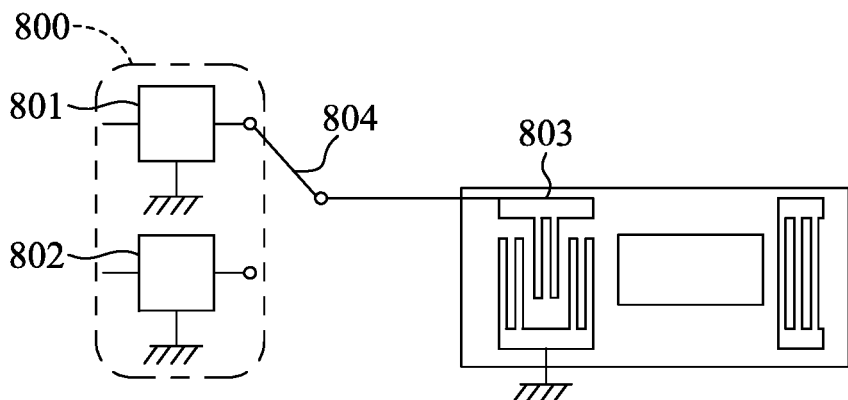
FIGS. 8A-8D are diagrams showing various electronic circuit modules for different single channel SH-SAW sensors in the present invention.

The electronic circuit module 800 in FIG. 8A includes two matching circuits 801 and 802, wherein the matching circuit 801 enables the IDT 803 to operate at frequency $f_1$, and the matching circuit 802 enables the IDT 803 to operate at frequency $f_2$. The electronic circuit module 800 further includes a switch 804 to select the matching circuit 801 or the matching circuit 802 for the IDT 803, so as to let the IDT 803 have multi-band characteristics. When the IDT 803 is connected to the matching circuit 801 via the switch 804, it can operate at frequency $f_1$. When the IDT 803 is connected to the matching circuit 802 via the switch 804, it can operate at frequency $f_2$ (e.g. $3f_1$).

Figure 8B:
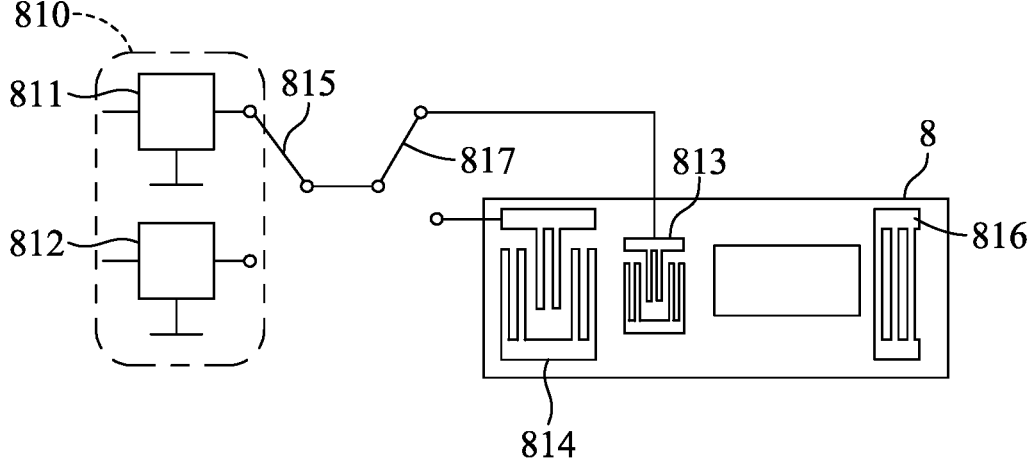

The SH-SAW sensor 8 in FIG. 8B has two IDTs 813, 814 and one reflector 816. The electronic circuit module 810 in FIG. 8B includes two matching circuits 811, 812 and two switches 815, 817, wherein the switch 815 can switch between the matching circuits 811, 812, and the switch 817 can switch between the IDTs 813, 814. The matching circuit 811 enables the IDT 813 to operate at frequency $f_1$, and the matching circuit 812 enables the IDT 814 to operate at frequency $f_2$. In this embodiment, the IDTs 813 and 814 have different center frequencies from each other. When the IDT 813 is connected to the matching circuit 811 via the switch 815 and the switch 817, it can operate at frequency $f_1$. Alternatively, when the IDT 814 is connected to the matching circuit 812 via the switch 815 and the switch 817, it can operate at frequency $f_2$.

Figure 8C:
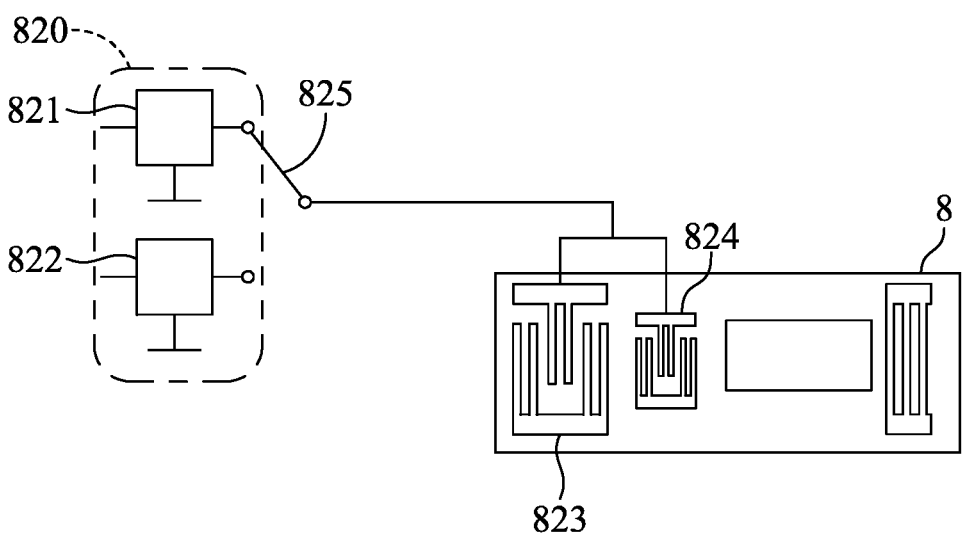

The SH-SAW sensor and the electronic circuit module 820 in FIG. 8C is identical to those in FIG. 8B. However, the connection between the electronic circuit module 820 and the SH-SAW sensor in FIG. 8C is different from that in FIG. 8B. In this embodiment, both of the IDT 823 and IDT 824 are connected to the same matching circuit 821 via the switch 825, when the switch 825 is connected to another matching circuit 822 during the subsequent measurement, both of the IDT 823 and IDT 824 are connected to the matching circuit 822 via the switch 825. By selecting different matching circuits, the IDT 823 and IDT 824 can operate at different frequencies during different measurements.

Figure 8D:
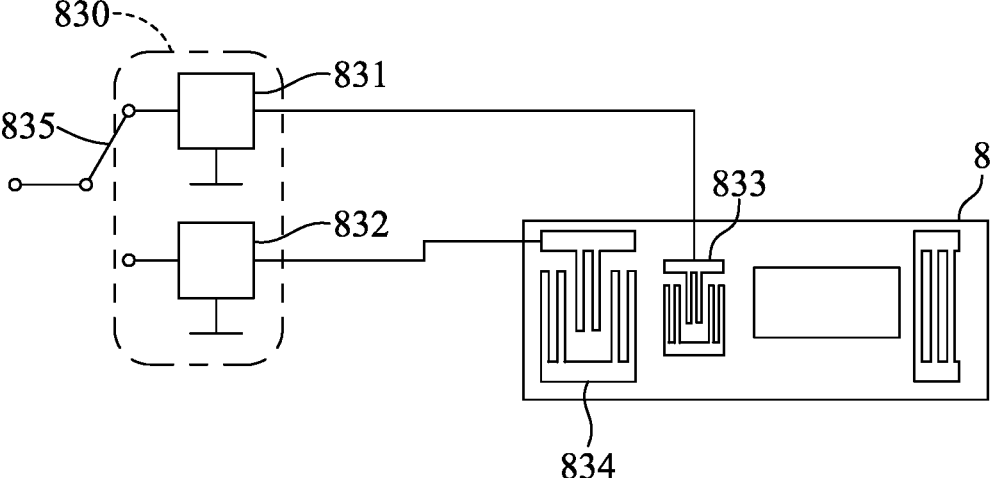

FIG. 8D shows a further configuration of the SH-SAW sensor and the electronic circuit module 830. The SH-SAW sensor and the electronic circuit module 830 in FIG. 8D is identical to those in FIG. 8B. However, the connection between the electronic circuit module 830 and the SH-SAW sensor in FIG. 8D is different from that in FIG. 8B. In this embodiment, the IDT 833 is always connected to the matching circuit 831 while the IDT 834 is always connected to the matching circuit 832, so as to enable the IDT 833 to operate at frequency $f_1$ and the IDT 834 to operate at frequency $f_2$. The switch 835 is connected to one end of the matching circuit 831 or the matching circuit 832 away from the SH-SAW sensor 8, to select the matching circuit 831 or the matching circuit 832 for the different frequencies.

Figure 9A:
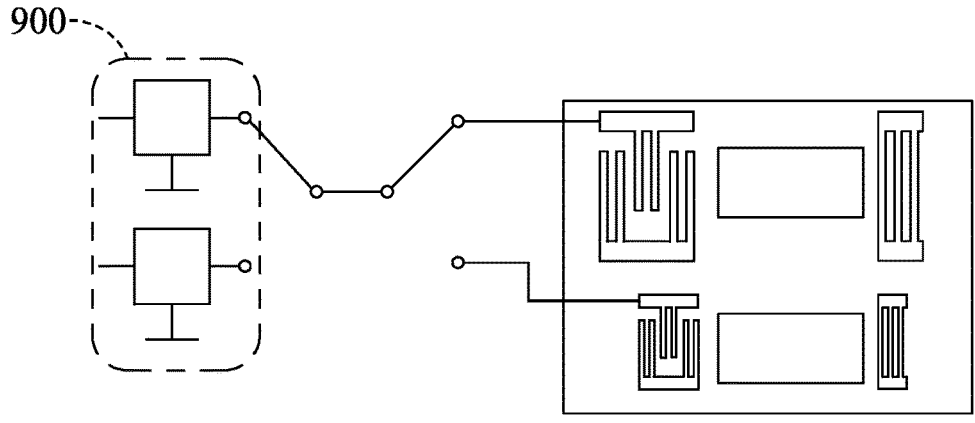
FIGS. 9A-9C are diagrams showing various electronic circuit modules for the multi-channel SH-SAW sensors in the present invention.
Figure 9B:
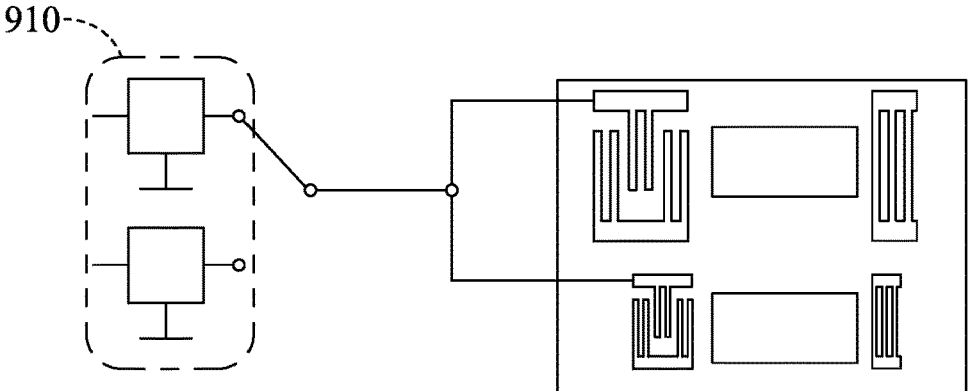
Figure 9C:
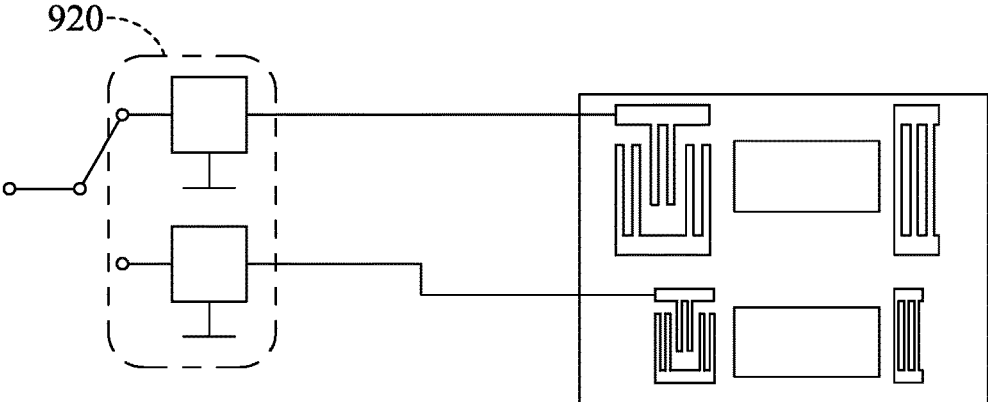

Please refer to FIG. 9A to FIG. 9C, which show various electronic circuit modules 900, 910, 920 for the multi-channel SH-SAW sensors. The connections between electronic circuit modules 900, 910, 920 and their corresponding SH-SAW sensor in FIGS. 9A-9C are similar to those in FIGS. 8B-8D, except that the SH-SAW sensors in FIGS. 9A-9C are multi-channel SH-SAW sensors. According to the present invention, the electronic circuit module including different matching circuits is configured to excite and detect SAWs with different frequencies, which is needed for the single channel SH-SAW sensor as shown in FIG. 5A and the multi-channel SH-SAW sensor with different frequencies as shown in FIG. 5B. However, such electronic circuit module is an optional configuration in the multi-channel SH-SAW sensor with different thicknesses, as shown in FIG. 5C.

In another aspect, the present invention provides a method for estimating respective amounts of different molecules in a biological liquid by using a SH-SAW sensor. This method enables the amounts of different molecules in a sample to be estimated in a quick and simple operation. Please refer to FIG. 10, which is a flow chart of a method 1000 for estimating amounts of different molecules by using a SH-SAW sensor at different frequencies, such as the single channel SH-SAW sensor in FIG. 5A and the multi-channel SH-SAW sensor with different frequencies in FIG. 5B in the present invention.

Figure 11A:
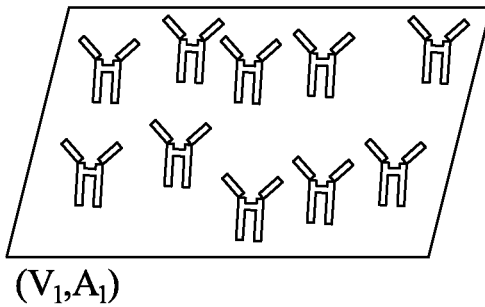
FIGS. 11A-11C are schematic diagrams showing the definitions of the parameters used in the method in FIG. 10.
Figure 11B:
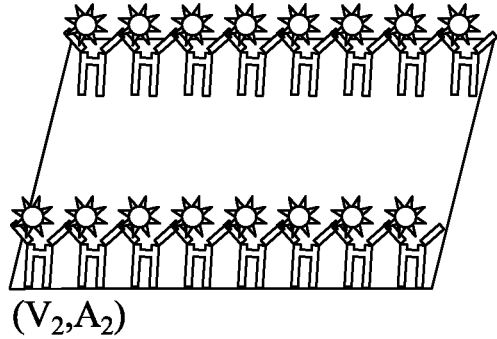

At the beginning of the method 1000, velocity and/or amplitude related parameters ($V_1$~$V_N$, $A_1$~$A_N$) for different molecules can be provided as known parameters in Step 1100. According to the schematic diagrams in FIGS. 11A and 11B, velocity and amplitude under a condition that the channel area of the SH-SAW sensor is coated with antibodies but not occupied by any molecule are calculated as ($V_1$, $A_1$), and velocity and amplitude under a condition that the channel area is completely occupied by a particular molecule are calculated as ($V_2$, $A_2$).

In order to capture the different molecules in the sample, one or more antibodies or probes are coated on the same channel area of the SH-SAW sensor. The antibodies or probes used in the SH-SAW sensor of the present invention include but not limiting to anti-ApoB100 antibody, anti-ApoA1 antibody, anti-ApoE antibody, anti-LP(a) antibody, anti-ApoB48 antibody, anti-C-reactive protein (CRP) antibody, anti-serum amyloid A (SAA) antibody, Severe Acute Respiratory Syndrome coronavirus 2 (SARS-CoV-2) antigen and a combination thereof.

In some specific case, some proteins have a common molecular, and the antibody for this common molecular can be coated on the channel area of the SH-SAW sensor in the present invention to capture these proteins simultaneously. For example, ApoB100 presents on chylomicron remnants, very low-density lipoproteins (VLDL), intermediate density lipoproteins (IDL), lipoprotein (a) (LP(a)) and LDL, and thus anti-ApoB100 antibody can be coated on the channel area of the SH-SAW sensor in the present invention to capture these lipoproteins.

Before applying the sample onto the SH-SAW sensor, usually, a buffer without the molecules will be applied onto the SH-SAW sensor. At this time, phase values for the SH-SAW sensor can be measured at different frequencies to be set as base-line for the phase value under a condition that the channel area is not occupied by any molecule. The measured phase values satisfy the following equation:

$$Pm(f_i) = 2\pi * f_i \frac{L_0}{V_1(f_i)}, \tag{1}$$

where i is an integer, $f_i$ is a specific frequency of the different frequencies, $L_0$ is the length of the channel area, $Pm(f_i)$ is a specific measured phase value of the measured phase values at the specific frequency under a condition that the channel area is not occupied by any molecule, and $V_1$ is the preconfigured velocity under the condition.

Figure 10:
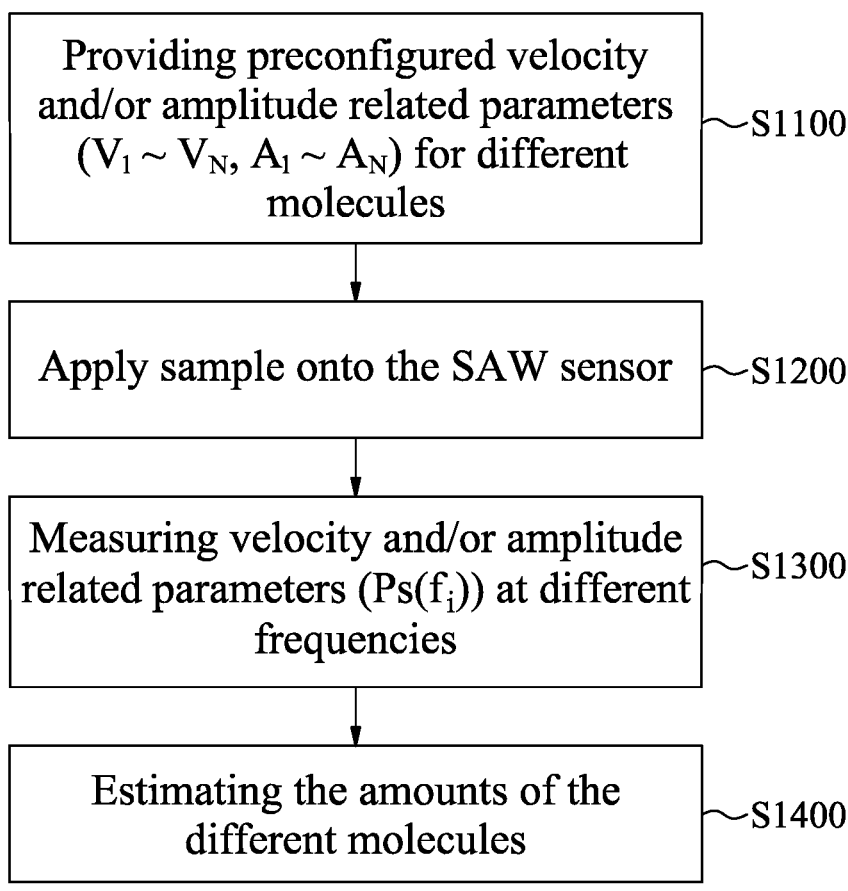
FIG. 10 is a flow chart of a method for estimating amounts of different molecules by using a SH-SAW sensor at different frequencies in the present invention.
Figure 11C:
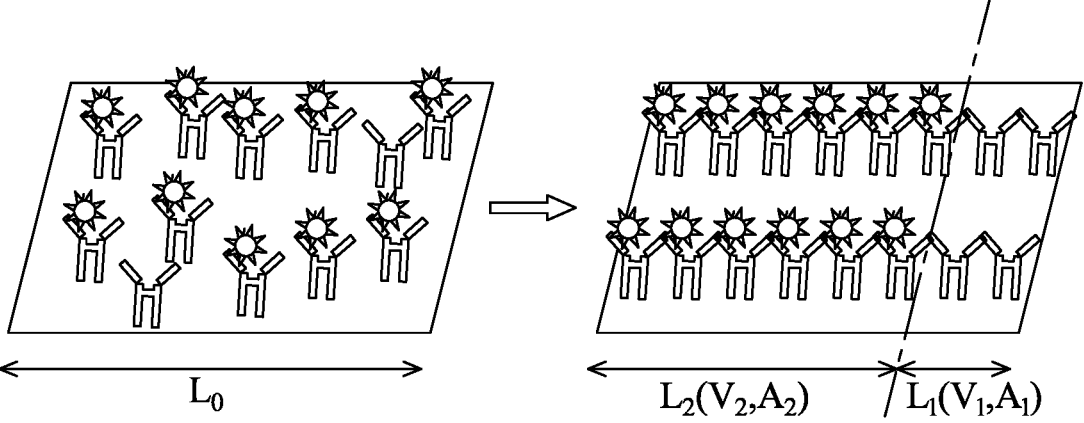

Please continue to refer to FIG. 10. In the next step S1200, the sample is applied onto the SH-SAW sensor to cause the different molecules in the sample to interact with the SH-SAW sensor. In an actual case, the molecular in the sample is captured by its specific antibody and randomly distributes on the channel area with a length $L_0$, as shown in left side of FIG. 11C. In the method of the present invention, the distribution of the molecule to be estimated is assumed as centralizing in one part of the channel area ($L_2$), as shown in right side of FIG. 11C, and the other part of the channel area ($L_1$) is assumed as not occupied by the molecule, wherein the length $L_2$ is proportional to the concentration of the molecule.

After applying the sample onto the SH-SAW sensor, velocity and/or amplitude related parameters are measured at different frequencies in Step 1300 of FIG. 10. Specifically, a phase shift for the specific channel (i.e. between input and output signals of the SH-SAW sensor) is measured at different frequencies. According to the present invention, Step 1300 is performed when the interaction of the SH-SAW sensor with the different molecules is complete, or is performed at a time interval after Step 1200. In Step 1400, the amounts of the different molecules are estimated according to the preconfigured velocity and/or amplitude related parameters obtained in Step 1100 as well as the measured velocity and/or amplitude related parameters obtained in Step 1300.

Figure 12:
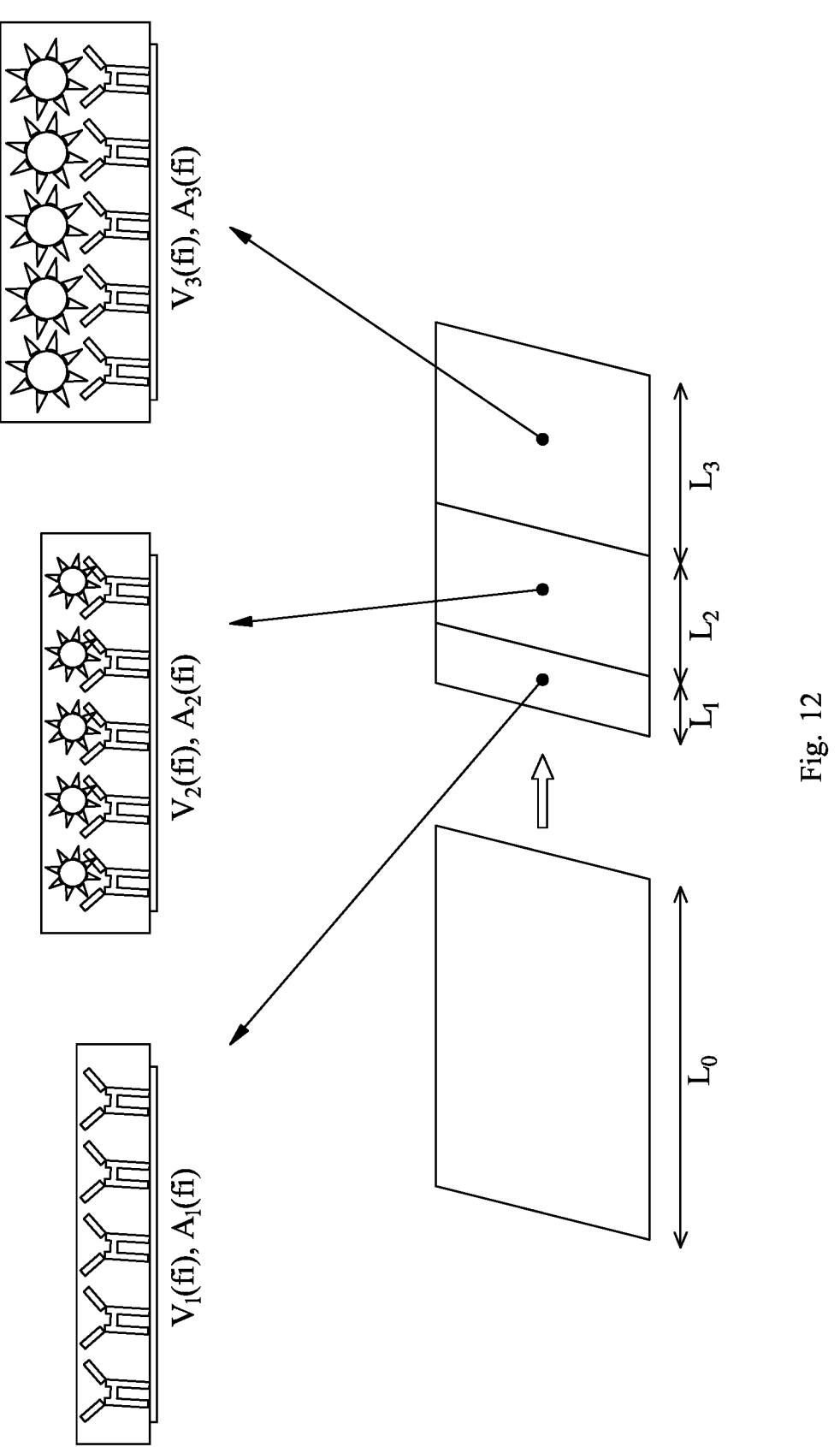
FIG. 12 is a schematic diagram showing the principle of the calculations in Step 1400 of FIG. 10.

According to the schematic diagram in FIG. 12, when the amounts of two different molecules in the sample are to be estimated, the distributions of the two molecules are assumed as centralizing in $L_2$ and $L_3$ of the channel area, respectively, and $L_1$ is assumed as not occupied by any molecule. On a condition that the channel area is at least partially occupied by the different molecules, the actual phase value for the SH-SAW sensor at a specific frequency is defined as $P(f_i)$ in the present invention. To obtain the unknown parameters $(L_1, L_2, L_3)$ that are proportional to the concentrations of the molecules, simultaneous equations built by specific phase values $P(f_i)$ and the measured phase values $Pm(f_i)$ are solved, wherein the measured phase values $Pm(f_i)$ is defined as the Equation (1) above and the specific phase values $P(f_i)$ satisfies an equation of $$P(f_i) = 2\pi * f_i \sum_{j=1}^{N} \frac{L_j}{Vj(fi)}, \tag{2}$$

where $f_i$ is a specific frequency of a SAW transmitted over the SH-SAW sensor, $P(f_i)$ is the specific phase value at the specific frequency under a condition that the channel area is at least partially occupied by the different molecules, i, j and N are integers with $N \geq 2$, $L_1 \sim L_N$ are equivalent partial distances of the specific channel respectively and $L_1$ can be zero, $L_1 + L_2 + \ldots + L_N = L_0$, at least $(L_2 + \ldots + L_N)/L_0$ of the channel area are covered by the different molecules with each equivalent partial distance corresponding to one of the different molecules, and $Vj(fi)$ is the preconfigured velocity under a condition that the channel area is not occupied by any molecule $(V_1)$ or that the channel area is completely occupied by a specific molecule $(V_2, V_3 \ldots)$, and wherein the simultaneous equations satisfy the following equation:

$$Ps(f_i) = Pm(f_i) - P(f_i) \tag{3}$$

$$= 2\pi * f_i \frac{L_0}{V_1(f_i)} - 2\pi * f_i \sum_{j=1}^{N} \frac{L_j}{Vj(fi)}$$

where i, j and N are integers with $N \geq 2$, $f_i$ is the specific frequency, and $Ps(f_i)$ is a specific phase shift between the specific measured phase value and the specific phase value at the specific frequency.

For example, on a condition that the channel area is at least partially occupied by two different molecules, there are three unknown parameters $(L_1, L_2, L_3)$ to be estimated. Accordingly, the simultaneous equations at three different frequencies $(f_1, f_2, f_3)$ are needed to be solved to obtain these three unknown parameters.

In still another aspect, the present invention provides a method for estimating respective amounts of different molecules in a biological liquid by using a SH-SAW sensor having at least two channels having different thicknesses. Please refer to FIG. 13, which is a flow chart of a method 2000 for estimating amounts of different molecules by using a SH-SAW sensor such as the multi-channel SH-SAW sensor with different thicknesses in FIG. 5C.

Figure 13:
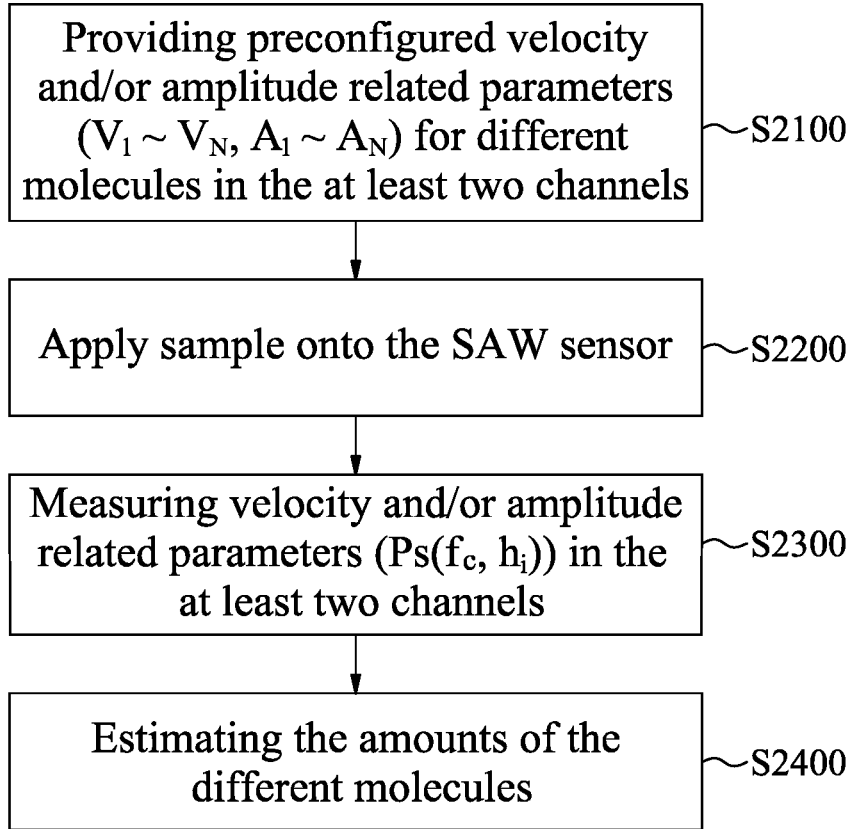
FIG. 13 is a flow chart of a method for estimating amounts of different molecules by using a SH-SAW sensor having different thicknesses in the present invention.

Similar to that in FIG. 10, velocity and/or amplitude related parameters $(V_1 \sim V_N, A_1 \sim A_N)$ for different molecules in the at least two channels can be calculated in Step 2100 of FIG. 13. In the next step S2200, the sample is applied onto the SH-SAW sensor to cause the different molecules in the sample to interact with the SH-SAW sensor. After applying the sample onto the SH-SAW sensor, velocity and/or amplitude related parameters in the at least two channels are measured in Step 2300. Finally, the amounts of the different molecules are estimated in Step 2400 according to the preconfigured velocity and/or amplitude related parameters obtained in Step 2100 as well as the measured velocity and/or amplitude related parameters obtained in Step 2300.

In the multi-channel SH-SAW sensor as shown in FIG. 5C, there are at least two channels, and each channel has a respective thickness different from those of the remaining channels. Because the thickness of a channel is relative to the wavelength of the SAWs propagating on the channel, the velocity of the SAWs is a function of the thickness of a channel at a constant frequency. In the following paragraphs, the preconfigured velocity of the SAWs in a channel with a specific thickness is represented as $V(h)$, where V is the velocity and h is the thickness.

In Step 2100 of FIG. 13, the preconfigured velocity and/or amplitude related parameters $(V_1 \sim V_N, A_1 \sim A_N)$ for different molecules in the at least two channels are obtained, and specific phase values $P(f_c, h_i)$ in the specific channel is derived by the following equation $$P(f_c, h_i) = 2\pi * f_c \sum_{j=1}^{N} \frac{L_j}{Vj(hi)}, \tag{4}$$

where $f_c$ is a constant frequency of the SAWs transmitted over the SH-SAW sensor, $h_i$ is a specific thickness of a specific channel of the at least two channels, $P(f_c, h_i)$ is the specific phase value at the constant frequency in the specific channel under a condition that the channel area of the specific channel is at least partially occupied by the different molecules, i, j and N are integers with $N \geq 2$, $L_1 \sim L_N$ are equivalent partial distances of the specific channel respectively and $L_1$ can be zero, $L_1 + L_2 + \ldots + L_N = L_0$, at least $(L_2 + \ldots + L_N)/L_0$ of the channel area are covered by the different molecules with each equivalent partial distance corresponding to one of the different molecules, and $Vj(hi)$ is the preconfigured velocity under a condition that the channel area is not occupied by any molecule $(j=1)$ or that the channel area is completely occupied by a specific molecule $(j>1)$.

Similarly, phase values for the at least two channels of the SH-SAW sensor can be measured by applying a buffer without the molecules onto the SH-SAW sensor. The measured phase values satisfy the following equation:

$$Pm(f_c, h_i) = 2\pi * f_c \frac{L0}{V1(hi)}, \tag{5}$$

where i is an integer, $f_c$ is the constant frequency of the SAWs transmitted over the SH-SAW sensor, $h_i$ is a specific thickness of a specific channel of the at least two channels, $L_0$ is the channel length, $Pm(f_c, h_i)$ is a specific measured phase value of the measured phase values at the constant frequency in the specific channel under a condition that the channel area is not occupied by any molecule, and $V_1(h_i)$ is the preconfigured velocity in the specific channel under the condition.

In Step 2300 of FIG. 13, phase shifts between input and output signals in the at least two channels are measured. Then, simultaneous equations built by specific phase values $P(f_c, h_i)$ and the measured phase values $Pm(f_c, h_i)$ are created and the amounts of the different molecules can be estimated by solving the simultaneous equations in Step 2400. The simultaneous equations satisfy the following equation:

$$Ps(f_c, h_i) = Pm(f_c, h_i) - P(f_c, h_i) \qquad (6)$$

$$= 2\pi * f_c \frac{L0}{V1(hi)} - 2\pi * f_c \sum_{j=1}^{N} \frac{Lj}{Vj(hi)},$$

where i, j and N are integers with N≥2, $f_c$ is the constant frequency, and $Ps(f_c, h_i)$ is a specific phase shift between the specific measured phase value and the specific phase value in the specific channel at the constant frequency.

Figure 14:
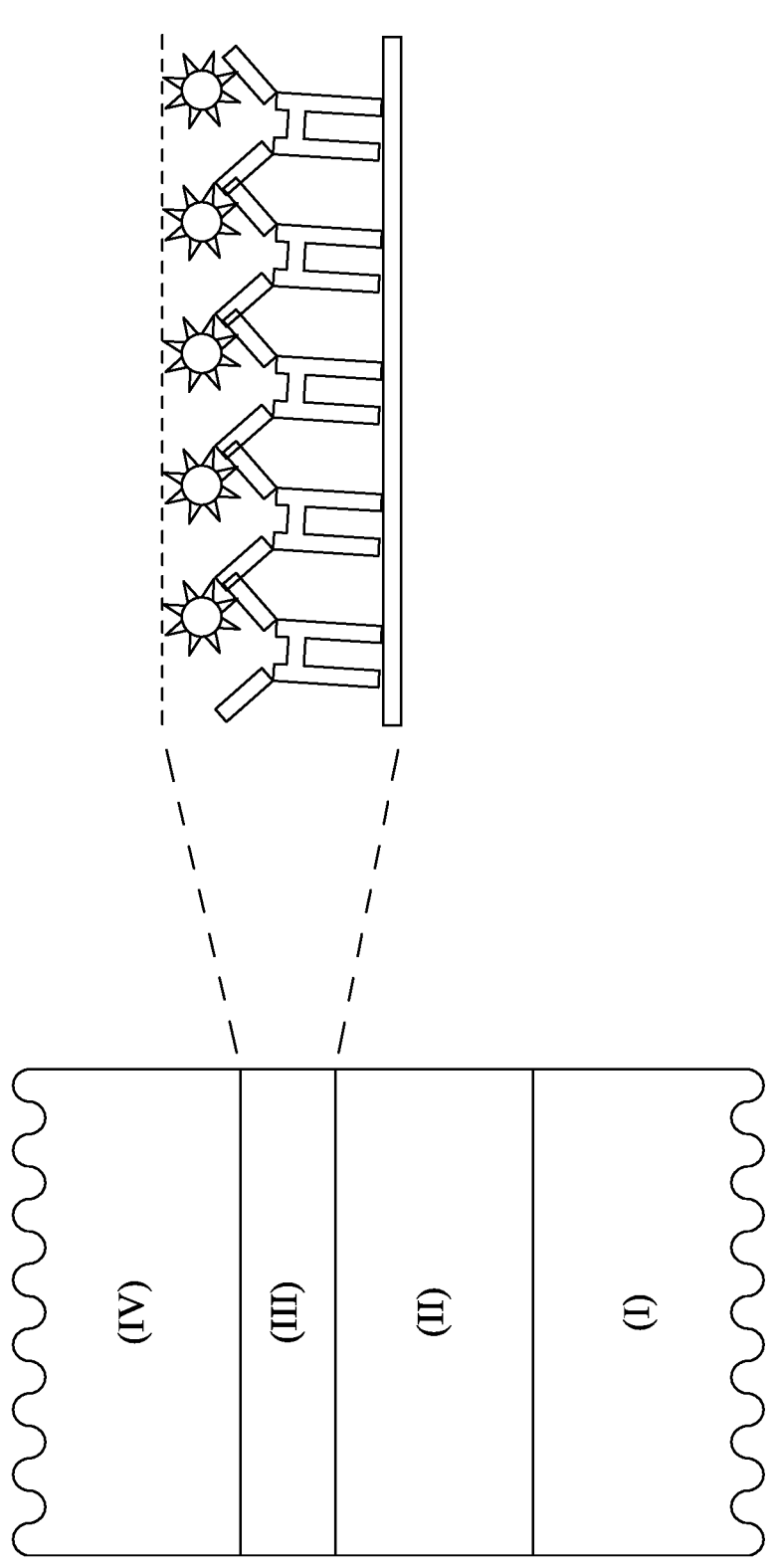
FIG. 14 is an enlarged diagram of the region R in FIG. 2 showing the layer structure of the SH-SAW sensor in the present invention.

FIG. 14 is an enlarged diagram of the region R in FIG. 2 showing the layer structure of the SH-SAW sensor. There are four layers when the sample is applied on the SH-SAW sensor, including a substrate (I), a metal layer (II), an bio-layer (III) and a liquid layer (IV). Preferably, the substrate (I) is a quartz substrate, and the metal layer (II) is a gold layer. As shown in FIG. 14, the bio-layer (III) is composed of the probe coated on the metal layer and particular molecules that are captured by the probe. As used herein, the term "thickness" refers to the thickness of the metal layer, the bio-layer or their combination. Preferably, the thickness of the surface area (e.g. including the metal layer and the bio-layer) of the SH-SAW sensor in the present invention ranges from 50~500 nm. Although the liquid layer (IV) is not shown in the region R in FIG. 2, it should be understood by the skilled person in the art that the particular molecules must be contained in a biological liquid.

By using the SH-SAW sensor and the methods in the present invention, the analyses for different molecules in a sample can be achieved in a simple operation. In addition, the present invention provides a faster approach to detect antigen-antibody reaction on the SH-SAW sensor in one-step than conventional assay.

These and other modifications and variations to the invention may be practiced by those of ordinary skill in the art without departing from the spirit and scope of the invention, which is more particularly set forth in the appended claims. In addition, it should be understood that aspects of the various embodiments may be interchanged in whole or in part. Furthermore, those of ordinary skill in the art will appreciate that the foregoing description is by way of example only, and it is not intended to limit the invention as further described in such appended claims. Therefore, the spirit and scope of the appended claims should not be limited to the exemplary description of the versions contained herein.

What is claimed is:

1. A method for estimating respective amounts of different molecules in a biological liquid by using a Shear Horizontal Surface Acoustic Wave (SH-SAW) sensor, comprising:

providing preconfigured velocity and/or amplitude related parameters of a plurality of SAWs transmitted over the SH-SAW sensor for the different molecules respectively;

causing the different molecules in the biological liquid to interact with the SH-SAW sensor;

measuring velocity and/or amplitude related parameters of the plurality of Surface Acoustic Waves (SAWs) for the SH-SAW sensor at different frequencies respectively after an interaction of the SH-SAW sensor with the different molecules; and estimating the respective amounts of the different molecules using the preconfigured velocity and/or amplitude related parameters as well as the measured velocity and/or amplitude related parameters.

2. The method as claimed in claim 1, wherein the SH-SAW sensor comprises at least one channel for a propagation of the plurality of SAWs, wherein the plurality of SAWs are transmitted at the different frequencies or the same frequency, each channel comprises at least one transducer, and the at least one transducer is one selected from a group consisting of a four fingers interdigital transducer (4F-IDT) having multi-band characteristics, a withdrawal weighted IDT having multi-band characteristics and an apodized weighted IDT having wide-band characteristics.

3. The method as claimed in claim 1, wherein the SH-SAW sensor comprises at least two channels for a propagation of the plurality of SAWs at the different frequencies.

4. The method as claimed in claim 2, wherein:

the least one channel includes a specific channel having a channel area and a channel length $L_0$ spanned between two transducers or between one transducer and a reflector of the SH-SAW sensor; and the step of providing preconfigured velocity and/or amplitude related parameters comprises a step of calculating preconfigured velocities of the plurality of SAWs for the different molecules.

5. The method as claimed in claim 4, further comprising the step of measuring phase values at the different frequencies respectively for the specific channel before causing the different molecules in the biological liquid to interact with the SH-SAW sensor, wherein the measured phase values satisfy the following equation:

$$Pm(f_i) = 2\pi * f_i \frac{L_0}{V_1(f_i)}$$

where i is an integer, $f_i$ is a specific frequency of the different frequencies, $L_0$ is the channel length, $Pm(f_i)$ is a specific measured phase value of the measured phase values at the specific frequency under a condition that the channel area is not occupied by any molecule, and $V_1$ is the preconfigured velocity under the condition.

6. The method as claimed in claim 5, wherein the step of measuring velocity and/or amplitude related parameters comprises the steps of:

measuring phase shifts at the different frequencies respectively for the specific channel; and estimating the respective amounts of the different molecules by solving simultaneous equations built by specific phase values for the preconfigured velocities and the measured phase values, wherein the specific phase values satisfies an equation of $$P(f_i) = 2\pi * f_i \sum_{j=1}^{N} \frac{L_j}{Vj(fi)},$$

where $f_i$ is the specific frequency of the SAWs transmitted over the SH-SAW sensor, $P(f_i)$ is the specific phase value at the specific frequency under a condition that the channel area is at least partially occupied by the different molecules, i, j and N are integers with N≥2, $L_1$~$L_N$ are equivalent partial distances of the specific channel respectively and $L_1$ can be zero, $L_1+L_2+ \ldots +L_N=L_0$, at least $(L_2+ \ldots +L_N)/L_0$ of the channel area are covered by the different molecules with each equivalent partial distance corresponding to one of the different molecules, and Vj(fi) is the pre-configured velocity under a condition that the channel area is not occupied by any molecule while j=1 or that the channel area is completely occupied by a specific molecule while j>1, and wherein the simultaneous equations satisfy the following equation:

$$Ps(f_i) = Pm(f_i) - P(f_i)$$

$$= 2\pi * f_i \frac{L_0}{V_1(f_i)} - 2\pi * f_i \sum_{j=1}^{N} \frac{L_j}{Vj(fi)}$$

where i, j and N are integers with $N \geq 2$, $f_i$ is the specific frequency, and Ps($f_i$) is a specific phase shift between the specific measured phase value and the specific phase value at the specific frequency.

7. The method as claimed in claim 2, wherein the step of measuring velocity and/or amplitude related parameters is performed when the interaction of the SH-SAW sensor with the different molecules is complete.

8. The method as claimed in claim 2, wherein the step of measuring velocity and/or amplitude related parameters is performed at a time interval after the step of causing the different molecules in the biological liquid to interact with the SH-SAW sensor.

9. A method for estimating respective amounts of different molecules in a biological liquid by using a Shear Horizontal Surface Acoustic Wave (SH-SAW) sensor, wherein the SH-SAW sensor has at least two channels having different thicknesses, comprising:

providing preconfigured velocity and/or amplitude related parameters of a plurality of Surface Acoustic Waves (SAWs) transmitted over the SH-SAW sensor for the different molecules in the at least two channels respectively;

causing the different molecules in the biological liquid to interact with the SH-SAW sensor;

measuring velocity and/or amplitude related parameters of the plurality of SAWs for the SH-SAW sensor in the at least two channels respectively after an interaction of the SH-SAW sensor with the different molecules; and estimating the respective amounts of the different molecules using the preconfigured velocity and/or amplitude related parameters as well as the measured velocity and/or amplitude related parameters.

10. The method as claimed in claim 9, wherein:

each of the least two channels includes a channel area and a channel length $L_0$ spanned between two transducers or between one transducer and a reflector of the SH-SAW sensor; and the step of providing preconfigured velocity and/or amplitude related parameters comprises a step of calculating preconfigured velocities of the plurality of SAWs for the different molecules in the at least two channels.

11. The method as claimed in claim 10, further comprising the step of measuring phase values for the at least two channels before causing the different molecules in the biological liquid to interact with the SH-SAW sensor, wherein the measured phase values satisfy the following equation:

$$Pm(f_c, h_i) = 2\pi * f_c \frac{L0}{V1(hi)}$$

where i is an integer, $f_c$ is a constant frequency of the SAWs transmitted over the SH-SAW sensor, $h_i$ is a specific thickness of a specific channel of the at least two channels, $L_0$ is the channel length, Pm($f_c$, $h_i$) is a specific measured phase value of the measured phase values at the constant frequency in the specific channel under a condition that the channel area is not occupied by any molecule, and $V_1(h_i)$ is the preconfigured velocity in the specific channel under the condition.

12. The method as claimed in claim 11, wherein the step of measuring velocity and/or amplitude related parameters comprises the steps of:

measuring phase shifts for the at least two channels respectively; and estimating the respective amounts of the different molecules by solving simultaneous equations built by specific phase values for the preconfigured velocities and the measured phase values, wherein the specific phase values satisfies an equation of $$P(f_c, h_i) = 2\pi * f_c \sum_{j=1}^{N} \frac{L_j}{Vj(hi)},$$

where $f_c$ is the constant frequency of the SAWs transmitted over the SH-SAW sensor, $h_i$ is a specific thickness of a specific channel of the at least two channels, P($f_c$, $h_i$) is the specific phase value at the constant frequency in the specific channel under a condition that the channel area of the specific channel is at least partially occupied by the different molecules, i, j and N are integers with $N \geq 2$, $L_1$~$L_N$ are equivalent partial distances of the specific channel respectively and $L_1$ can be zero, $L_1+L_2+ \ldots +L_N=L_0$, at least $(L_2+ \ldots +L_N)/L_0$ of the channel area are covered by the different molecules with each equivalent partial distance corresponding to one of the different molecules, and Vj(hi) is the preconfigured velocity under a condition that the channel area is not occupied by any molecule while j=1 or that the channel area is completely occupied by a specific molecule while j>1, and wherein the simultaneous equations satisfy the following equation:

$$Ps(f_c, h_i) = Pm(f_c, h_i) - P(f_c, h_i) = 2\pi * f_c \frac{L0}{V1(hi)} - 2\pi * f_c \sum_{j=1}^{N} \frac{Lj}{Vj(hi)}$$

where i, j and N are integers with $N \geq 2$, $f_c$ is the constant frequency, and Ps($f_c$, $h_i$) is a specific phase shift between the specific measured phase value and the specific phase value in the specific channel at the constant frequency.

13. The method as claimed in claim 9, wherein each channel of the SH-SAW sensor comprises a sensing area having a respective thickness different from those of the remaining channels, and the respective thickness ranges from 50~500 nm.

\* \* \* \* \*